US005756747A

United States Patent [19]

Gerster

[11] Patent Number: 5,756,747
[45] Date of Patent: May 26, 1998

[54] 1H-IMIDAZO[4,5-C]QUINOLIN-4-AMINES

[75] Inventor: John F. Gerster, St. Paul, Minn.

[73] Assignee: Riker Laboratories, Inc., St. Paul, Minn.

[21] Appl. No.: 455,273

[22] Filed: May 31, 1995

Related U.S. Application Data

[63] Continuation of Ser. No. 70,262, Jun. 2, 1993, which is a continuation-in-part of Ser. No. 316,035, Feb. 27, 1989, abandoned.

[51] Int. Cl.$^6$ .................................................. C07D 671/04
[52] U.S. Cl. .................................................. 546/82
[58] Field of Search ..................... 514/293; 546/82, 546/159

[56] References Cited

U.S. PATENT DOCUMENTS

| | | | |
|---|---|---|---|
| 4,552,874 | 11/1985 | Mardin et al. | 514/222 |
| 4,689,338 | 8/1987 | Gerster | 514/293 |
| 4,698,346 | 10/1987 | Musser et al. | 514/293 |
| 4,698,348 | 10/1987 | Gerster | 514/293 |
| 4,929,624 | 5/1990 | Gerster et al. | 514/293 |

OTHER PUBLICATIONS

J. Org. Chem. 15, 1278–1284 (1950) (Bachman et al.).
J. Med. Chem. 11, pp. 87–92 (1968) (Jain et al.).
Chem. Abs. 85, 94362 (1976).
J. Heterocyclic Chem. 18, 1537–1540 (1981) (Berenyi et al.).

*Primary Examiner*—C. Warren Ivy
*Assistant Examiner*—Evelyn Huang
*Attorney, Agent, or Firm*—MarySusan Howard; Ted K. Ringsred; Walter N. Kirn

[57] ABSTRACT

Novel 1H-imidazo[4,5-c]quinolin-4-amines are disclosed. The compounds function as antiviral agents and they are potential synthetic intermediates in the preparation of known antiviral agents and labeled known antiviral agents. Processes for the preparation of the compounds, methods for their antiviral use, and methods of inducing interferon biosynthesis, are also described.

1 Claim, No Drawings

1H-IMIDAZO[4,5-C]QUINOLIN-4-AMINES

CROSS REFERENCE TO RELATED APPLICATION

This is a continuation of application Ser. No. 08/070,262 filed Jun. 2, 1993, pending.

BACKGROUND OF THE INVENTION

1. Field of the Invention

This invention pertains to 1H-imidazo[4,5-c]-quinoline compounds. More particularly this invention pertains to antiviral 1H-imidazo[4,5-c]quinoline-4-amine compounds, intermediates for the preparation of such compounds, pharmaceutical compositions containing such compounds, and pharmacological methods of using such compounds.

2. Description of the Related Art

The first reliable report of the 1H-imidazo[4,5-c]-quinoline ring system, Backman et al., *J. Org. Chem.* 15, 1278–1284 (1950), describes the synthesis of 1-(6-methoxy-8-quinolinyl)-2-methyl-1H-imidazo[4,5-c]-quinoline for possible use as an antimalarial agent. Subsequently, syntheses of various substituted 1H-imidazo[4,5-c]quinolines have been reported. For example, Jain et al., *J. Med. Chem.* 11, pp. 87–92 (1968), has synthesized the compound 1-[2-(4-piperidyl)ethyl]-1H-imidazo[4,5-c]quinoline as a possible anticonvulsant and cardiovascular agent. Also, Baranov et al., *Chem. Abs.* 85, 94362 (1976), has reported several 2-oxoimidazo[4,5-c]quinolines, and Berenyi et al., *J. Heterocyclic Chem.* 18, 1537–1540 (1981), has reported certain 2-oxoimidazo[4,5-c]-quinolines.

Certain 1H-imidazo[4,5-c]quinolin-4-amines are described in U.S. Pat. No. 4,689,338. These compounds are substituted on the 1-position by alkyl, hydroxyalkyl, acyloxyalkyl, benzyl, phenylethyl or substituted phenylethyl and are useful as antiviral agents. Furthermore, these compounds are known to induce interferon biosynthesis.

SUMMARY OF THE NOVEL INVENTION

This invention provides novel 1H-imidazo-[4,5-c] quinolin-4-amines. These compounds function as antiviral agents, and they are potential synthetic intermediates in the preparation of known antiviral agents and labeled known antiviral agents. This invention also provides processes for preparing such compounds, pharmaceutical compositions containing such compounds, and pharmacological methods of using such compounds.

DETAILED DESCRIPTION OF THE INVENTION

This invention provides compounds of Formula I:

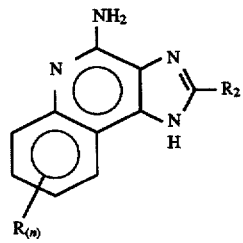

wherein $R_2$ is selected from the group consisting of hydrogen, straight chain or branched chain alkyl containing one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to about four carbon atoms, straight chain or branched chain alkoxy containing one to about four carbon atoms, and halogen, with the proviso that when the benzene ring is substituted by two such moieties, then the moieties together contain no more than 6 carbon atoms; and each R is independently selected from the group consisting of straight chain or branched chain alkoxy containing one to about four carbon atoms, halogen, and straight chain or branched chain alkyl containing one to about four carbon atoms, and n is an integer from zero to 2, with the proviso that if n is 2, then said R groups together contain no more than 6 carbon atoms; or a pharmaceutically acceptable acid addition salt thereof.

For the purpose of the instant specification and claims, the term "lower" when used in conjunction with "alkyl" or "alkoxy" designates straight chain or branched chain substituents containing 1 to about 4 carbon atoms.

When R is alkoxy it is preferably methoxy.

When $R_2$ is alkyl it is preferably lower alkyl.

Other substituents that contain an alkyl radical (e.g., R when R is alkyl, or lower alkyl or lower alkoxy substituents on a benzene ring in $R_2$) preferably contain one or two carbon atoms in each alkyl radical.

The halogen substituents are selected from fluorine, chlorine and bromine. Preferred halogen substituents are fluorine and chlorine.

It is preferred that n of Formula I be zero or one. It is most preferred that n of Formula I be zero.

Presently preferred compounds are: 1H-imidazo[4,5-c] quinolin-4-amine; 2-phenylmethyl-1H-imidazo[4,5-c] quinolin-4-amine; and pharmaceutically acceptable acid addition salts thereof.

A compound of the invention of Formula I can be prepared as described in Scheme I illustrated below, wherein R, $R_2$ and n are as defined above and $R_1$ is a substituent capable of being subjected to an elimination or like reaction to afford a 1H-imidazo[4,5-c]quinolin-4-amine. $R_1$ can be any substituent that can be removed. Examples of general classes of $R_1$ include groups that will yield a stable cation upon treatment with aqueous acid (e.g. tertiary substituents, meaning for the purposes of the instant specification and claims any substituent wherein the carbon atom bonded to the 1-nitrogen is fully substituted with electron-donating groups, for example hydroxy, alkoxy, acyloxy, halogen, alkyl, phenyl, and the like) and substituents from which the 1H-imidazo[4,5-c]quinolin-4-amine can be eliminated (e.g. 2-hydroxyalkyl groups). Such $R_1$ substituents include 1,1-dimethylethyl (i.e., t-butyl), 1,1-dimethyl-2-hydroxyethyl, 2-hydroxy-1-phenyl-1-methylethyl, 1,1-dimethyl-2-hydroxypropyl, and the like.

Many quinolines of Formula III are known compounds (see, for example, U.S. Pat. No. 3,700,674 and references cited therein). Those that are not known can be prepared by known methods, for example, from 4-hydroxy-3-nitroquinolines as illustrated in step (1) of Scheme I. Step (1) can be conducted by reacting the 4-hydroxy-3-nitroquinoline of Formula II with phosphorus oxychloride. The reaction is preferably conducted in N,N-dimethylformamide and is preferably accompanied by heating. Preferably, a large molar excess of phosphorus oxychloride is avoided. Use of about 1–2 moles of phosphorus oxychloride per mole of the 4-hydroxy-3-nitroquinoline of Formula II has been found to be particularly preferable.

In step (2) a 3-nitro-4-chloroquinoline of Formula III is reacted by heating with a compound of the formula $R_1NH_2$, wherein $R_1$ is as defined above, in a

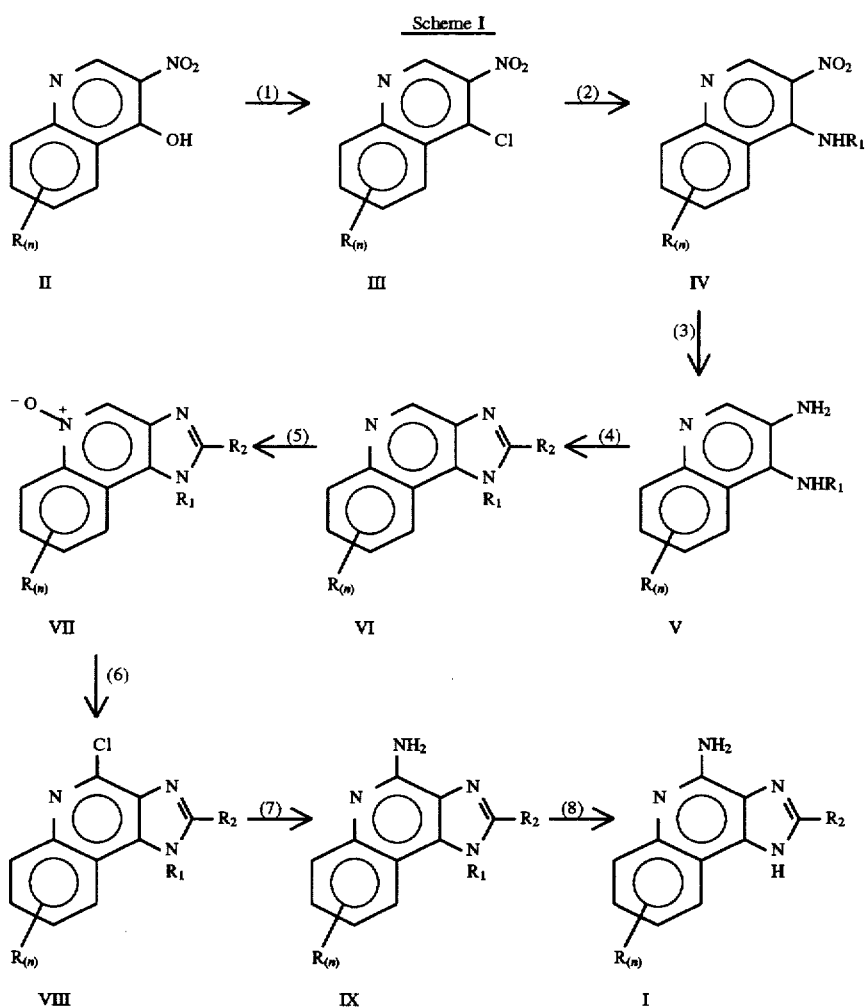

Scheme I suitable solvent such as dichloromethane, water, or tetrahydrofuran, to provide a quinoline of Formula IV. Some of the compounds of Formula IV are novel.

Steps (1) and (2) can be combined such that the 3-nitro-4-chloroquinoline need not be isolated prior to reaction with $R_1NH_2$. Such a reaction is exemplified in Example 134 and Example 188 (Step A) of U.S. Pat. No. 4,689,338, the disclosure of which is incorporated herein by reference.

A compound of Formula IV is reduced in step (3) preferably using a catalyst such as platinum on charcoal, to provide a compound of Formula V. The reduction can be carried out conveniently on a Paar apparatus in an inert solvent such as toluene or a lower alkanol. Some compounds of Formula V are novel.

In step (4) an intermediate compound of Formula V is reacted with (i) a 1,1-dialkoxyalkyl alkanoate such as diethoxymethyl acetate, or (ii) a carboxylic acid that will introduce the desired $R_2$ group, or (iii) a trialkyl ortho ester of the formula $R_2C(Oalkyl)_3$, wherein "alkyl" is an alkyl group containing 1 to about 4 carbon atoms, or (iv) a combination of such a carboxylic acid with such a trialkyl ortho ester to provide a compound of Formula VI. The reaction can be carried out by heating, e.g., at about 130° C., in the presence of an acid, preferably an alkanoic acid having one more carbon atom than $R_2$. Some of the compounds of Formula VI are novel.

Step (5) provides an intermediate of Formula VII. First, the hydroxy group, if one is present in $R_1$, is protected with, for example, an alkanoyloxy group such as acetoxy, or with benzoyloxy. Such protecting groups and reactions for their placement and removal are well known to those skilled in the art. See, for example, U.S. Pat. No. 4,689,338, Examples 115 to 123. The resulting protected compound is then oxidized with a conventional oxidizing agent that is capable of forming N-oxides. Preferred oxidizing agents include peroxyacids and hydrogen peroxide. The oxidation reaction is preferably conducted in glacial acetic acid. Heating is generally employed to accelerate the rate of reaction.

In step (6) an N-oxide of Formula VII is first heated in the presence of a suitable chlorinating agent such as phosphorus oxychloride to provide an intermediate of Formula VIII. It is preferred that phosphorus oxychloride be used in combination with a solvent (e.g., dichloromethane) inert to conventional chlorinating agents. It is also possible to run the reaction in the presence of a catalytic amount of N,N-dimethylformamide. The second part of step (6) involves removal of the protecting group, if one is present, by methods well known to those skilled in the art. When the protecting group is acetyl, hydrolysis with ammonia in methanol is preferred.

In step (7) the 4-chloro group is replaced by a 4-amino group to provide a compound of Formula IX. The reaction is carried out in the presence of ammonium hydroxide or, preferably, ammonia. Preferably the intermediate of Formula VIII is heated at 125° to 175° C. under pressure for 6-24 hours. Preferably the reaction is conducted in a sealed reactor in the presence of either ammonium hydroxide or a solution of ammonia in an alkanol, (e.g., 15% ammonia in methanol).

In step (8), a compound of Formula IX is heated in the presence of aqueous acid to effect the deamination of the $R_1$ group, thus providing a 1H-imidazo[4,5-c]-quinolin-4-amine of Formula I. Preferred conditions for the reaction include brief (e.g., 30 minute) reflux in dilute (e.g. 4N) aqueous hydrochloric acid.

Two alternate routes for the preparation of a compound of the invention are shown in Scheme II, wherein R, $R_1$, $R_2$ and n are as defined above. In step (1) of Scheme II, a compound of Formula VII is reacted with a reagent such as acetic anhydride and undergoes a rearrangement reaction to afford a 4-hydroxy compound of Formula X. Other suitable reagents for the conversion include tosyl chloride, or various acyl halides such as acetyl chloride, in the presence of hydroxide (e.g. potassium hydroxide, sodium hydroxide, calcium hydroxide, and the like). Also, the transformation can be carried out by reaction with boron trifluoride followed by heating with phosphoric acid.

Step (2) of Scheme II illustrates the transformation of a compound of Formula X to a compound of Formula XI by first removing the protecting group, if one is present, from the 1-substituent. For example, if $R_1$ contains a hydroxy group, this group will have been acylated in the previous step. $R_1$ is then removed by heating with dilute aqueous acid (e.g., 4N to 6N acid) as described above in connection with step (8) of Scheme I. A compound of Formula XI can then be converted in step (3) to a compound of Formula XIII by reaction with a suitable chlorinating agent such as thionyl chloride, phosgene, oxalyl chloride, phosphorus pentachloride, and the like, or preferably phosphorus oxychloride. The reaction can be carried out in an appropriate solvent or in the absence of solvent. Mild heating (e.g., at about 100° C.) is preferred. In step (4), a compound of Formula XIII is converted to a compound of Formula I as discussed above in connection with step (7) of Scheme I.

A second alternative route shown in Scheme II for preparing a compound of Formula I begins with a compound of Formula XII, some of which have been reported in East German Patent 242,806-A1, the disclosure of which is incorporated herein by reference. As shown in step (5)

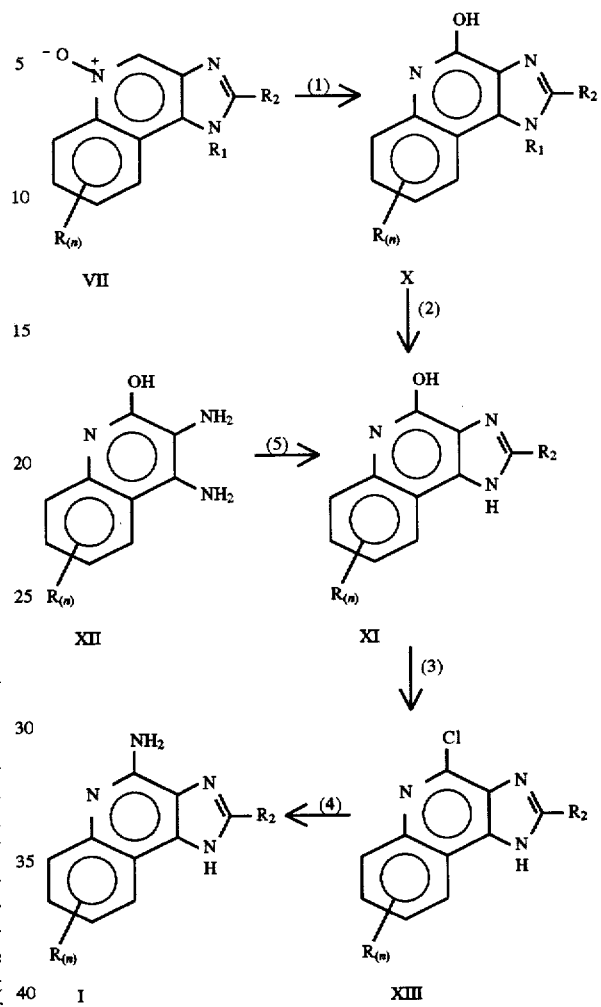

of Scheme II, a compound of Formula XII can be reacted as described above in connection with step (4) of Scheme I to provide a compound of Formula XI. A compound of Formula XI, in turn, can be converted, also as discussed above, to a compound of Formula I.

A further alternate route for the preparation of a compound of Formula I is shown in Scheme III, wherein R, $R_2$, and n are as defined above.

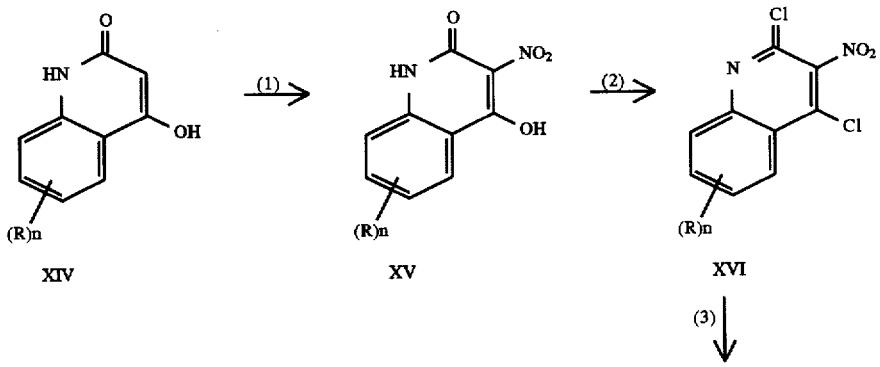

-continued
SCHEME III

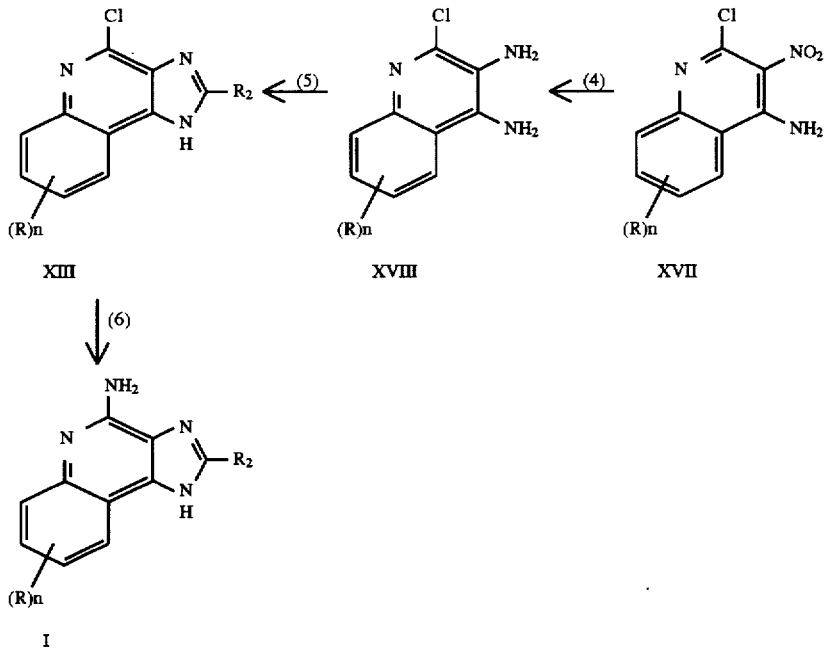

The unsubstituted compound of Formula XIV, 4-hydroxy-2(1H)-quinolinone, is a known, commercially available compound, and other compounds of Formula XIV can be prepared therefrom by methods known to those skilled in the art. For example, Chem. Ber., 1927, 60, 1108 (Koller), discloses the preparation of 7-chloro-4-hydroxy-2(1H)-quinolinone, and J. Heterocyclic Chem. 1988, 25, 857 (Kappe et al.) discloses 4-hydroxy-2(1H)-quinolinones with, e.g., 5,8-dichloro substitution, 6,8-dichloro substitution, and 7-chloro-8-methoxy substitution. The disclosure of the above-cited articles is incorporated herein by reference.

In step (1) of Scheme III a compound of Formula XIV is nitrated at the 3-position using conventional nitration methods. It is known to those skilled in the art, however, that nitration is not necessarily selective. For example, depending on the particular R substituents in a compound of Formula XIV and the particular conditions employed, nitration might occur on the benzo ring of a compound of Formula XIV. Those skilled in the art, however, are able to select appropriate conditions that will afford a compound of Formula XV. Preferred conditions involve the use of mild heating (e.g., at about 40° C.) with acetic acid as the solvent. The unsubstituted compound of Formula XV, 4-hydroxy-3-nitro-2(1H)-quinolinone is known and the preparation thereof is disclosed in Chem Ber. 1918, 51, 1500 (Gabriel), the disclosure of which is incorporated herein by reference.

In step (2) the nitrated compound of Formula XV is chlorinated with a suitable chlorinating agent such as thionyl chloride, phosgene, oxalyl chloride, phosphorus pentachloride, and the like, or preferably phosphorus oxychloride to provide the dichloride product of Formula XVI. The reaction can be carried out in an inert solvent or if appropriate in neat chlorinating agent. Mild heating serves to accelerate the rate of reaction. Preferred conditions involve reaction in neat phosphorus oxychloride with heating at about 100° C. The unsubstituted compound of Formula XVI, 2,4-dichloro-3-nitroquinoline, is known and the preparation thereof is disclosed in Gabriel cited above.

In step (3), a compound of Formula XVI is substituted at the 4-position by reaction with an excess of ammonia in methanol (e.g., a solution of 15 percent ammonia by weight in methanol). It is preferred to use gentle heating (e.g., 50° C.). This reaction proceeds selectively, affording primarily the 4-substituted product and a minor amount of the 2-amino compound. In step (4), a compound of Formula XVII is reduced to afford a compound of Formula XVIII. This reduction can be carried out by conventional methods such as by electrochemical reduction, by reaction with metals such as zinc, tin, or iron in acid, by reaction with sodium dihydro(trithio)borate, and by other conventional single step or multi-step methods (e.g., via the hydroxylamine intermediate) known to those skilled in the art. Preferred reduction conditions include conventional homogeneous or preferably heterogeneous catalytic hydrogenation conditions. A compound of Formula XVIII is suspended or preferably dissolved in a solvent such as ethanol, ethyl acetate, methanol, isopropyl alcohol, or mixtures thereof with acetic acid, in the presence of a suitable heterogeneous hydrogenation catalyst such as a platinum or rhodium on alumina, palladium on carbon, platinum on carbon, or the like under hydrogen pressure (e.g., 1–5 atm) in a steel bomb.

In step (5), a compound of Formula XVIII is reacted as described above in connection with step (4) of Scheme I to afford a compound of Formula XIII.

In step (6), a compound of Formula XIII converted to a compound of Formula I as described above in connection with step (7) of Scheme I.

A compound of Formula I can be used as an antiviral agent itself or it can be used in the form of a pharmaceutically acceptable acid-addition salt such as a hydrochloride, dihydrogen sulfate, trihydrogen phosphate, hydrogen nitrate, methane sulfonate or a salt of another pharmaceutically acceptable acid. A pharmaceutically acceptable acid-addition salt of a compound of Formula I can be prepared, generally by reaction of the compound with an equimolar, amount of a relatively strong acid, preferably an inorganic acid such as hydrochloric, sulfuric, or phosphoric acid, or an organic acid such as methanesulfonic acid, in a polar solvent. Isolation of the salt is facilitated by the addition of a solvent, such as diethyl ether, in which the salt is insoluble.

A compound of the invention can be formulated for the various routes of administration in any known, pharmaceutically acceptable vehicle such as water or polyethylene glycol. Suitable formulations for topical application generally contain less than 10% by weight of a compound of Formula I, and will preferably contain about 0.1% to 5% by weight of a compound of Formula I.

A compound of the invention can be administered in water containing either a surfactant such as "Tween 80" or cellulose. A 5% concentration of the surfactant is generally useful in topical, oral and intraperitoneal formulations. Formulations for topical administration include, for example, a cream containing 1% by weight of the preferred antiviral compound in micronized form (i.e., particle size of 1–2 microns in diameter); 0.2% by weight of methyl paraben; 0.02% by weight of propyl paraben; 5% by weight of "Avicel CL-611" (a colloidal form of microcrystalline cellulose which has been coprocessed with sodium carboxymethyl cellulose (available from FMC Corporation, Philadelphia, Pa.); and 93.78% by weight of water. The formulation can be prepared by dry-mixing the antiviral compound with the "Avicel CL-611", and then combining that mixture with a solution containing the methyl paraben and propyl paraben in the water.

Further formulations that might find use include those formulations disclosed in commonly assigned copending application Ser. No. 07/284,933, wherein isostearic and/or oleic acid is used as a skin penetration enhancer for sustained release creams, ointments, end adhesive-coated sheet materials containing 1-isobutyl-1H-imidazo[4,5-c]quinolin-4-amine.

The compounds of the invention exhibit antiviral activity in mammals and can therefore be used to control viral infections. A preferred use of a compound of the invention is as an agent to control infections in mammals caused by Type I or Type II Herpes simplex virus. Generally, treatment is effective when a compound of Formula I or a formulation thereof is administered topically (e.g., intravaginally or on the skin), to a herpes infection. Compounds of Formula I can also be used to treat a herpes infection by oral, subcutaneous, or intraperitoneal administration.

The anti-Herpes activity of the compounds of Formula I relative to primary lesions caused by Type I or Type II Herpes simplex virus can be demonstrated using the method described generally by Kern, et al., Antimicrob. Agents Chemother. 14, 817–823 (1978).

This method uses female guinea pigs of 200 to 300 grams in weight, preferably 200 to 260 grams in weight. Hartley guinea pigs are the preferred strain. The guinea pigs are anesthetized with pentobarbital or methoxyflurane, and then infected intravaginally, using a cotton swab, with about $10^5$ plaque forming units of Herpes simplex virus, either type I or type II. A compound of Formula I is formulated preferably in saline or water using a surfactant such as "Tween 80" (a polyoxyethylene sorbitan monooleate, commercially available from Emulsion Engineering Inc., Elk Grove Village, Ill.). Alternatively, a compound of Formula I can be formulated in "PEG 400" (a polyethyleneglycol of average molecular weight of about 400, commercially available from Union Carbide Corporation), or in polyethyleneglycol cream. Application of the formulation is initiated at the predetermined interval after infection such as one hour after infection. The formulation is applied intravaginally, for example, twice daily for a predetermined number of days, typically five or seven days. Virus replication can be monitored by determining the amount of virus recovered with vaginal swabs taken, for example, on days 1, 2, 3, 5 or 7 after infection. Virus is eluted from the swab in 1 mL of cell growth medium (Medium 199, Gibco Laboratories, Grand Island, N.Y.) and virus titer is determined using cell monolayers. External lesions are scored daily for 10 days using the following scale: zero, no lesions; 1, redness or swelling; 2, a few small vesicles; 3, several large vesicles; 4, large ulcers and necrosis; 5, paralysis. The degree of inhibition of lesion development is determined by comparing lesion development in infected and untreated or vehicle-treated control animals to lesion development in infected and drug-treated animals. Comparison studies with known drugs such as phosphonacetic acid and acyclovir can also be conducted. The compounds of the invention reduce the number of lesions and the severity thereof.

I believe that the antiviral activity exhibited by the compounds of the invention is attributable to induction of interferon biosynthesis. Some of the compounds of Formula I induce the biosynthesis of interferon in human blood cells in culture. The compounds 2-phenylmethyl-1H-imidazo[4,5-c]quinolin-4-amine and 1H-imidazo[4,5-c]quinolin-4-amine, for example, induce interferon biosynthesis when tested according to the method set forth below.

Interferon Induction in Human Blood Cells in Culture

This method is based on an assay described by H. Kirchner, Ch. Kleinicke and W. Digel in "A Whole-Blood Technique for Testing Production of Human Interferons by Leukocytes", Journal of Immunological Methods, 48: 213–219, 1982, incorporated herein by reference.

Activity is based on the measurement of interferon secreted into culture media. Interferon is measured by bioassay.

Whole blood is collected by venipuncture into EDTA($K_3$) vacutainer tubes. Blood is diluted 1:10 with RPMI 1640 media supplemented with 25 mM HEPES (N-2-hydroxyethylpiperazine-N'-2-ethansulfonic acid) and L-glutamine with 1% penicillin-streptomycin solution added (available from GIBCO, Grand Island, N.Y.). 200 µL portions of diluted blood are added to 96 well (flat bottom) MicroTest™ tissue culture plates (available from Falcon Plastics, Oxnard, Calif.).

Test compounds are solubilized in ethanol or DMSO then diluted with distilled water, 0.01N sodium hydroxide, or 0.01N hydrochloric acid (The choice of solvent will depend on the chemical characteristics of the compound being tested). It is preferred that the final concentration of either ethanol or DMSO does not exceed 1%. A compound is initially tested at concentrations of 0.5, 2.5 and 5.0 µg/mL. The assay is repeated using higher concentrations if necessary.

The solution of test compound is added in a volume (less than or equal to 50 µL) to the wells containing 200 µL of diluted whole blood. Solvent and/or media is added to control wells (wells with no test compound) and as needed to adjust the final volume of each well to 250 µL. The plates are covered with plastic lids, vortexed gently and then incubated for 48 hours at 37° C. with a 5% carbon dioxide atmosphere.

Following incubation, the plates are covered with parafilm and then centrifuged at 1000 rpm for 15 minutes at 4° C. in a Damon IEC Model CRU-5000 centrifuge. Media (about 150 μL) is removed from 4 to 8 wells and is pooled into 2 mL sterile freezing vials. Samples are maintained at −70° C. until analysis.

Samples are shipped on dry ice to Lee Biomolecular Research Laboratories, Inc., San Diego, Calif. Interferon is determined by bioassay, A549 human lung carcinoma cells challenged with encephalomyocarditis. The details of the bioassay method used by Lee Biomolecular have been described by G. L. Brennan and L. H. Kronenberg in "Automated Bioassay of Interferons in Micro-test Plates", BioTechniques, June/July, 78, 1983, incorporated herein by reference. Interferon dilutions and A549 cells are incubated at 37° C. for 12 to 24 hours. The incubated cells are infected with an inoculum of encephalomyocarditis. The infected cells are incubated for an additional period at 37° C. before quantifying the viral cytopathic effect. The viral cytopathic effect is quantified by staining followed by spectrophotometric absorbance measurements. The interferon assay may be either a type I assay in which cells are seeded in 96 well plates and grown to "confluence" prior to exposure to interferon dilutions or a type II assay in which cells are seeded directly into wells containing interferon dilutions. Results are expressed as alpha reference units/mL based on the value obtained for NIH IF-L standard.

That biosynthesis of interferon is induced suggests that at least certain compounds of the invention would be useful in treating other diseases such as rheumatoid arthritis, warts, eczema, Hepatitis B, psoriasis, multiple sclerosis, essential thrombocythaemia, cancer such as basal cell carcinoma, and other neoplastic diseases.

Some 1-substituted-1H-imidazo[4,5-c]quinolin-4-amines, such as those described in U.S. Pat. No. 4,689,338, are known antiviral agents. A further utility for the compounds of the invention therefore lies in their use as intermediates in the preparation of such known antiviral agents. A compound of Formula I can be readily converted to a known antiviral agent by methods well known to those skilled in the art. For example, a compound of Formula I can be converted to a metal salt of the 1-nitrogen, for instance by treatment with sodium hydride in a polar solvent such as N,N-dimethylformamide, and reacted with an alkylating agent (e.g., an alkyl halide) to provide a compound substituted at the 1-position.

The following examples are provided to illustrate the invention and are not intended to be limiting thereof.

EXAMPLE 1

Preparation of a Compound of Formula IV

To a stirred solution of 67.1 g (0.322 mole) of 4-chloro-3-nitroquinoline in 800 mL of dichloromethane was added 54 mL (0.38 mole) of triethylamine and 96 mL (0.96 mole) of 2-amino-2-methyl-1-propanol. The mixture was heated at reflux for one hour, then stirred at about 20° C. for about 16 hours. The mixture was concentrated by evaporation in vacuo and the residue was slurried in 1.5 l of water. The product was separated by filtration and dried to provide solid 2,2-dimethyl-2-[(3-nitro-4-quinolinyl)amino]ethanol. The structural assignment was confirmed by comparison of the nuclear magnetic resonance spectrum to that of a sample which was previously used for elemental analysis. Analysis of earlier sample: Calculated for $C_{13}H_{15}N_3O_2$: % C, 59.8; % H, 5.8; % N, 16.1; Found % C, 59.9; % H, 5.8; % N, 16.1.

EXAMPLE 2

Preparation of a Compound of Formula V

To a solution of 35 g (0.134 mole) of 2,2-dimethyl-2-[(3-nitro-4-quinolinyl)amino]ethanol (from Example 1) in 1.2 l of ethyl acetate was added 35 g of magnesium sulfate and about 2 g of 5% platinum on charcoal, and the mixture was hydrogenated on a Parr apparatus until no further reaction occurred. Filtration followed by evaporation in vacuo provided a residue which was yellow solid 2-[(3-amino-4-quinolinyl)amino]-2,2-dimethylethanol.

EXAMPLE 3

Preparation of a Compound of Formula VI

A crude reaction product obtained by the method of Example 2 of 0.39 mole of 2-[(3-amino-4-quinolinyl)-amino]-2,2-dimethylethanol was mixed with 77.2 mL of diethoxymethyl acetate, and the resulting mixture was heated on a steam bath for 0.75 hour. Evaporation provided a residue which was diluted with 500 mL of water. The solid was separated by filtration and washed with water to provide light yellow crystals of beta,beta-dimethyl-1H-imidazo[4,5-c]quinoline-1-ethanol. When a sample of this compound from another preparation was recrystallized from ethyl acetate it had a melting point of 211°–216° C. Analysis: Calculated for $C_{14}H_{15}N_3O$: % C, 69.7; % H, 6.3; % N, 17.4; Found: % C, 70.0; % H, 6.3; % N, 17.4.

EXAMPLE 4

Acetylation and N-Oxidation of a Compound of Formula VI

A mixture of 67.8 g (0.281 mole) of beta,beta-dimethyl-1H-imidazo[4,5-c]quinoline-1-ethanol and 170 mL of acetic anhydride was heated at about 100° C. for three hours. To this solution was added 1700 mL of methanol and the solution was refluxed for about 0.5 hour. The solution was evaporated in vacuo and the residue was basified with a saturated sodium bicarbonate solution. Scratching provided an off-white solid which was separated by filtration, washed with water and dissolved in chloroform. The solution was dried over magnesium sulfate and concentrated to a solid residue. The solid was dissolved in 750 mL of chloroform. To this solution was added 67.3 g (0.312 mole) of meta-chloroperbenzoic acid. The mixture was stirred for three hours, evaporated, then washed with saturated sodium bicarbonate solution. Sodium chloride was added, then the mixture was extracted with chloroform. The organic layer was then dried over magnesium sulfate and concentrated by evaporation in vacuo to provide 1-(2-acetoxy-1,1-dimethylethyl)-1H-imidazo[4,5-c]quinoline-5-oxide.

EXAMPLE 5

Preparation of a Compound of Formula VIII

Step A

To a stirred mixture of 76.6 g (0.256 mole) of 1-(2-acetoxy-1,1-dimethylethyl)-1H-imidazo[4,5-c]-quinoline-5-oxide in 0.75 liters of dichloromethane was added in portions 43.2 g of phosphorus oxychloride. The reaction was exothermic. The reaction mixture was allowed to cool on standing and stirred for 4 hours. The mixture was evaporated in vacuo. The residue was neutralized with a saturated sodium bicarbonate solution, and that solution was filtered to separate the solid product. The product was dissolved in dichloromethane. The organic layer was washed with water, dried over magnesium sulfate and evaporated in vacuo. The light brown solid was assumed to be the expected 4-chloro compound, 1-(2-acetoxy-1,1-dimethylethyl)-4-chloro-1H-imidazo[4,5-c]quinoline.

Step B

The solid from Step A was added to 750 mL of 17% ammonia in methanol and 75 mL of ammonium hydroxide. After stirring for about 64 hours the mixture was evaporated in vacuo, the residue was slurred with saturated sodium bicarbonate solution and the solid residue was collected by filtration. The solid was washed with water and dried providing 4-chloro-beta,beta-dimethyl-1H-imidazo[4,5-c]quinoline-1-ethanol. The structural assignment was confirmed by nuclear magnetic resonance spectral analysis. When a sample of this compound from another run was recrystallized from ethanol it had a melting point of 207°–210° C. Analysis: Calculated for $C_{14}H_{14}N_3OCl$: % C, 61.0; % H, 5.1; % N, 15.2; Found: % C, 61.2; % H, 5.1; % N, 15.2.

EXAMPLE 6

Preparation of a Compound of Formula IX

A sample of 4.1 g of the deacetylated product from Step B of Example 5 was combined with 75 mL of a solution of 18% ammonia in methanol in a sealed reactor and heated at 150° C. for six hours. The mixture was cooled to about 20° C., then the crystalline product was separated by filtration. The solid product was washed by slurring in a solution of saturated sodium bicarbonate, separated by filtration, washed with water and dried. The solid was recrystallized from methanol, treating with decolorizing charcoal, to provide colorless crystals of 4-amino-beta, beta-dimethyl-1H-imidazo[4,5-c]quinoline-1-ethanol, m.p. 277°–281° C. Analysis: Calculated for $C_{14}H_{16}N_4O$: % C, 65.5; % H, 6.3; % N, 21.9; Found: % C, 65.6; % H, 6.3; % N, 21.7.

EXAMPLE 7

Preparation of a Compound of Formula VI

A mixture of 26.7 g (0.115 mole) of 2-[(3-amino-4-quinolinyl)amino]-2,2-dimethyl-1-ethanol and 42.8 g (0.180 mole) of triethyl orthophenylacetate was heated at 130° C. for four hours. The mixture was diluted with water, acidified to pH 5 with 6N hydrochloric acid and diluted with diethyl ether. The solid which precipitated was separated by filtration, rinsed with diethyl ether and slurred in saturated sodium bicarbonate solution. The solid was separated by filtration and dried to provide beta, beta-dimethyl-2-phenylmethyl-1H-imidazo[4,5-c]quinoline-1-ethanol. The structural assignment was confirmed by nuclear magnetic resonance spectral analysis.

EXAMPLE 8

Preparation of a Compound of Formula VII

Using the method described in Example 4, the product from Example 7, 2,2-dimethyl-(2-phenylmethyl-1H-imidazo[4,5-c]quinoline)-1-ethanol was acetylated to provide 1-(2-acetoxy-1,1-dimethylethyl)-2-phenylmethyl-1H-imidazo[4,5-c]quinoline which was oxidized to provide solid 1-(2-acetoxy-1,1-dimethylethyl)-2-phenylmethyl-1H-imidazo[4,5-c]quinoline-5-oxide.

EXAMPLE 9

Preparation of a Compound of Formula VIII

Using the method described in Example 5, Parts A and B, the product from Example 8, 1-(2-acetoxy-1,1-dimethylethyl)-2-phenylmethyl-1H-imidazo[4,5-c]-quinoline-5-oxide was chlorinated to provide 4-chloro-1-(2-acetoxy-1,1-dimethylethyl)-2-phenylmethyl-1H-imidazo[4,5-c]quinoline which was deacetylated to provide 4-chloro-beta,beta-dimethyl-2-phenylmethyl-1H-imidazo[4,5-c]quinoline-1-ethanol. Recrystallization from ethyl acetate gave tan crystals, m.p. 262°–266° C. Analysis: Calculated for $C_{21}H_{20}N_3OCl$: % C, 68.9; % H, 5.5; % N, 11.5; Found: % C, 68.6; % H, 5.5; % N, 11.3.

EXAMPLE 10

Preparation of a Compound of Formula I

Step A

The method described in Example 6 except 13% ammonia in methanol was used to aminate 4-chloro-beta,beta-dimethyl-2-phenylmethyl-1H-imidazo[4,5-c]quinolin-1-ethanol from Example 9 to provide 2-(4-amino-2-phenylmethyl-1H-imidazo[4,5-c]quinoline)-2,2-dimethyl-1-ethanol.

Step B

To the 4-amino compound from Step A above was added 100 mL of 20% hydrochloric acid and the mixture was heated at reflux for three hours. The mixture was cooled to about 20° C., the solid precipitate was separated by filtration to provide 2-phenylmethyl-1H-imidazo[4,5-c]quinolin-4-amine hydrochloride.

Step C

The hydrochloride salt from Step B was slurred in saturated sodium bicarbonate solution. The free base was a solid and was separated by filtration and dried. Recrystallization from ethanol provided solid 2-phenylmethyl-1H-imidazo[4,5-c]quinolin-4-amine, m.p. 274°–277° C. Analysis: Calculated for $C_{17}H_{14}N_4$: % C, 74.4; % H, 5.1; % N, 20.4; Found: % C, 73.8; % H, 5.2; % N, 20.1.

EXAMPLE 11

Preparation of a Compound of Formula IV

A solution of 19 g (0.10 mole) of 4-hydroxy-3-nitroquinoline, 200 mL of dichloromethane, 10 mL of N,N-dimethylformamide and 10 mL of phosphorus oxychloride was stirred at about 20° C. for 30 minutes and then heated at its reflux temperature for 30 minutes. The solution was cooled to about 20° C. and diluted with 300 mL of diethyl ether. This solution was stirred for 30 minutes at 20° C., treated with decolorizing charcoal and filtered through celite. The filtrate was washed repeatedly with 200 mL portions of cold sodium bicarbonate solution until foaming stopped and the washings were basic. The solution containing 4-chloro-3-nitroquinoline was dried over magnesium sulfate and filtered and evaporated in vacuo. To the solid was added a mixture of 20 g of tertiary-butylamine and 100 mL of N,N-dimethylformamide and the mixture was heated on a steam bath for about one hour. To this mixture was added about 200 mL of water and the product was isolated by filtration and recrystallized from hexane to provide N-(1,1-dimethylethyl)-3-nitro-4-quinolinamine, m.p. 106°–108° C. Analysis: Calculated for $C_{13}H_{15}N_3O_2$: % C, 63.7; % H, 6.2; % N, 17.1; Found: % C, 64.0; % H, 6.3; % N, 17.1.

EXAMPLE 12

Preparation of a Compound of Formula VI

A mixture of 17.7 g (0.0722 mole) of N-(1,1-dimethylethyl)-3-nitro-4-quinolinamine, 350 mL of ethyl acetate, 20 g of magnesium sulfate and about one gram of platinum on charcoal was hydrogenated on a Paar apparatus.

After hydrogen pressure stabilized, the mixture was filtered and the filtrate was evaporated to provide a solid residue of 3-amino-N-(1,1-dimethylethyl)-4-quinolinamine.

To the solid was added 20 mL (0.12 mole) of diethoxymethyl acetate and the solution was heated on a steam bath for one hour. The solution was cooled to about 20° C., diluted with water and basified with concentrated ammonium hydroxide. After standing for about 0.5 hour the mixture was extracted with diethyl ether, the extracts were dried over magnesium sulfate and the mixture was filtered. The filtrate was evaporated to dryness and the oily residue gradually solidified. The residue was slurred and washed in hexane, the product was separated by filtration and dried to provide light orange solid 1-(1,1-dimethylethyl)-1H-imidazo[4,5-c]quinoline, melting point after recrystallization from diethyl ether 145°–147° C. Analysis: Calculated for $C_{14}H_{15}N_3$: % C, 74.5; % H, 6.7; % N 18.7; Found: % C, 74.6; % H, 6.7; % N, 18.6.

EXAMPLE 13

Preparation of a Compound of Formula VII

To a solution of 23.5 g (0.104 mole) of 1-(1,1-dimethylethyl)-1H-imidazo[4,5-c]quinoline in 200 mL of chloroform was added 23.4 g (0.115 mole) of meta-chloroperbenzoic acid. The mixture was stirred at about 20° C. for 24 hours. The solution was basified with saturated sodium bicarbonate solution, then dried over magnesium sulfate. Filtration of the mixture, followed by evaporation in vacuo provided a cream colored solid. The solid residue was slurred in dilute ammonium hydroxide, then filtered, washed with water and dried, to provide white solid 1-(1,1-dimethylethyl)-1H-imidazo[4,5-c]quinoline-5-oxide.

EXAMPLE 14

Preparation of a Compound of Formula VIII

Using the method of Example 5, Step A, 1-(1,1-dimethylethyl)-1H-imidazo[4,5-c]quinoline-5-oxide was chlorinated to provide 4-chloro-1-(1,1-dimethylethyl)-1H-imidazo[4,5-c]quinoline which was recrystallized from diethyl ether. Analysis: Calculated for $C_{14}H_{14}ClN_3$: % C, 64.7; % H, 5.4; % N, 16.2; Found: % C, 64.9; % H, 5.4; % N, 16.1.

EXAMPLE 15

Preparation of a Compound of Formula IX

Using the method of Example 10, Step A, 4-chloro-1-(1,1-dimethylethyl)-1H-imidazo[4,5-c]-quinoline was aminated to provide 1-(1,1-dimethylethyl)-1H-imidazo[4,5-c]quinolin-4-amine. Recrystallization from a mixture of ethanol and dichloromethane provided colorless crystals, m.p. 275°–285° C. (dec). Analysis: Calculated for $C_{14}H_{16}N_4$: % C, 70.0; % H, 6.7; % N, 23.3; Found: % C, 70.1; % H, 6.8; % N, 23.4.

EXAMPLE 16

Preparation of a Compound of Formula I

A mixture of 1.5 g (0.0062 mole) of 1-(1,1-dimethylethyl)-1H-imidazo[4,5-c]quinolin-4-amine and 25 mL of 6N hydrochloric acid was heated at its reflux temperature for 30 minutes. The mixture was filtered hot and the precipitate was slurred in saturated sodium bicarbonate solution. The solid was again separated by filtration, washed with water and dried. Recrystallization from ethanol provided colorless (white) crystals of 1H-imidazo[4,5-c]quinolin-4-amine, m.p. greater than 300° C.

EXAMPLE 17

Preparation of a Compound of Formula XI

A mixture of 1.5 g (0.086 mole) of known compound 2-hydroxy-3,4-quinolinediamine and 10 mL of diethoxymethyl acetate was heated at 125° C. for 0.5 hours. The mixture was diluted with 25 mL of water, then the mixture was basified with concentrated ammonium hydroxide. The product was separated by filtration, washed with water and ethanol and dried. Recrystallization from a mixture of water and N,N-dimethylformamide provided colorless solid 1H-imidazo[4,5-c]quinolin-4-ol. Analysis: Calculated for $C_{10}H_7N_3O$: % C, 64.9; % H, 3.8; % N, 22.7; Found: % C, 64.5; % H, 3.9; % N, 22.3.

EXAMPLE 18

Preparation of a Compound of Formula XIII

A mixture of 500 mg of 1H-imidazo[4,5-c]quinolin-4-ol and about 6 mL of phosphorous oxychloride was heated on a steam bath for about 16 hours, then poured over ice. The mixture was neutralized with saturated sodium bicarbonate solution, then the solid was separated by filtration. The solid was dissolved in dilute hydrochloric acid, the mixture was filtered and the filtrate was neutralized with concentrated ammonium hydroxide to reprecipitate the product. Filtration and drying was followed by recrystallization from methanol to provide crystals of 4-chloro-1H-imidazo[4,5-c]-quinoline. Analysis: Calculated for $C_{10}H_6N_3$: % C, 59.0; % H, 3.0; % N, 20.6; Found: % C, 59.5; % H, 3.0; % N, 20.2.

EXAMPLE 19

Alternate Preparation of a Compound of Formula I

Using the method of Example 6, the product of Example 18, 0.2 g (0.0010 mole) of 4-chloro-1H-imidazo[4,5-c]quinoline was aminated at 175° C. in 12% ammonia in methanol to provide 1H-imidazo[4,5-c]quinolin-4-amine. The structure was verified by comparison of infrared and nuclear magnetic resonance spectra of the product with spectra of the product from Example 23.

EXAMPLES 20–23

According to the general methods of EXAMPLES 17–19, 2-hydroxy-3,4-quinolinediamine could be reacted with triethylorthoracetate, triethylorthopropionate, triethylorthobutyrate, or triethylorthopentanoate, and subsequently chlorinated and aminated to ultimately afford 2-methyl-1H-imidazo[4,5-c]quinolin-4-amine (Example 20), 2-ethyl-1H-imidazo[4,5-c]quinolin-4-amine (Example 21), 2-propyl-1H-imidazo-[4,5-c]quinolin-4-amine (Example 22), or 2-butyl-1H-imidazo[4,5-c]-quinolin-4-amine (Example 23), respectively.

EXAMPLES 24–26

Reaction of a Compound of Formula I

EXAMPLE 24

To a stirred suspension of 1.0 g (0.0054 mole) of 1H-imidazo[4,5-c]quinolin-4-amine in 10 mL of N,N- dimethylformamide was added 0.15 g (0.0059 mole) of sodium hydride. To this stirred mixture was added 0.6 mL (0.0054 mole) of benzyl chloride. After 15 minutes the mixture was heated at about 100° C. for 45 minutes. The mixture was diluted with 20 mL of water. A solid was separated by filtration, then recrystallized from ethanol, treating with decolorizing charcoal. The product was white crystals of 1-phenylmethyl-1H-imidazo[4,5-c]quinolin-4-amine, m.p. 255°–260° C. Analysis: Calculated for $C_{17}H_{14}N_4$: % C, 74.4; % H, 5.1; % N, 20.4; Found: % C, 73.9; % H, 5.2; % N, 20.4.

EXAMPLE 25

To a stirred suspension of 1.0 g (0.0054 mole) of 1H-imidazo[4,5-c]quinolin-4-amine in 10 mL of N,N-dimethylformamide was added 0.15 g (0.0059 mole) of sodium hydride. To this stirred mixture was added 0.74 g (0.0054 mole) of isobutyl bromide. After 30 minutes the mixture was heated at about 100° C. for one hour. The mixture was cooled to about 20° C., diluted with 20 mL of water, and the solid was separated by filtration. Recrystallization from N,N-dimethylformamide provided the known antiviral agent 1-(2-methylpropyl)-1H-imidazo[4,5-c]quinolin-4-amine.

EXAMPLE 26

To a stirred suspension of 5.0 g (0.0271 mole) of 1H-imidazo[4,5-c]quinolin-4-amine in 50 mL of N,N-dimethylformamide was added 0.9 g (0.0299 mole) of sodium hydride. To this mixture was added 5.6 g (0.0271 mole) of ethyl 4-bromobutyrate. After stirring for 40 minutes the mixture was heated on a steam bath for one hour. The mixture was added to 100 g of ice and stirred. The yellow solid was separated by filtration and dried to provide ethyl (4-amino-1H-imidazo[4,5-c]-quinoline-1)butyrate.

EXAMPLE 27

Preparation of a Compound of Formula I

A stirred mixture of 5.6 g (0.022 mole of 4-amino-beta,beta-dimethyl-1H-imidazo[4,5-c]quinoline-1-ethanol and 150 mL of 20% hydrochloric acid was heated for one hour, cooled to about 20° C. and filtered to separate the solid product. The solid was slurred in aqueous ammonium hydroxide, filtered and dried. Recrystallization from ethanol with treatment with decolorizing charcoal provided white crystals of 1H-imidazo[4,5-c]quinolin-4-amine, m.p. greater than 300° C. The structural assignment was supported by infrared and nuclear magnetic resonance spectral analyses and comparison to the product from another preparation which had an analysis for $C_{10}H_8N_4$: % C 65.2; % H, 4.4; % N, 30.4; Found: % C, 64.8; % H, 4.4; % N, 30.2.

EXAMPLE 28

Alternate Preparation of a Compound of Formula XI

Step A

To a stirred mixture of 34.2 g (0.142 mole) of beta,beta-dimethyl-1H-imidazo[4,5-c]quinolin-1-ethanol (from Example 3) in 200 mL of acetic acid was added 29 mL (0.284 mole) of 30% hydrogen peroxide and the mixture was heated at 65° C. for about 10 hours. The mixture was evaporated in vacuo, the residue was diluted with 200 mL of water and then basified with sodium bicarbonate solution. The precipitate was separated by filtration, washed with water and dried to provide light yellow solid 1-(2-hydroxy-1,1-dimethyl)-1H-imidazo[4,5-c]quinoline-5-oxide.

Step B

A mixture of 28.8 g (0.112 mole) of 1-(2-hydroxy-1,1-dimethylethyl)-1H-imidazo[4,5-c]-quinolin-5-oxide and 100 mL of acetic anhydride was heated on a steam bath for 6 hours, cooled to about 20° C. and filtered. The solid which was obtained was rinsed with acetic anhydride, then diethyl ether to provide light gray solid 1-(2-acetoxy-1,1-dimethylethyl)-1H-imidazo[4,5-c]quinolin-4-ol. The structural assignment was supported by infrared and nuclear magnetic resonance spectral analyses.

Step C

A solution of 18.1 g (0.0605 mole) of 1-(2-acetoxy-1,1-dimethylethyl)-1H-imidazo[4,5-c]quinolin-4-ol and 500 mL of 6N hydrochloric acid was heated at its reflux temperature for one day and cooled to about 20° C. The solid salt, 1H-imidazo[4,5-c]quinolin-4-ol hydrochloride, was separated by filtration. The salt was neutralized by slurring in saturated sodium bicarbonate solution. The solid was separated by filtration, dried, and further dried by twice repeated coevaporation with ethanol to provide tan solid 1H-imidazo[4,5-c]quinolin-4-ol. The structural assignment was supported by infrared and nuclear magnetic resonance spectral analyses and comparison with the spectra of the product from Example 17.

EXAMPLE 29

Alternate Preparation of a Compound of Formula XIII

Step A

To 50 mL of acetic anhydride was added 11.5 g (0.0477 mole) of 1-(1,1-dimethylethyl)-1H-imidazo-[4,5-c]quinoline-5-oxide (product of Example 13) and the slurry was heated on a steam bath for a few minutes, then allowed to cool to about 20° C. The solid was separated by filtration and washed with an ethanol-hexane mixture. Slurring with dilute ammonium hydroxide, filtration and washing with water provided solid which has recrystallized from an ethanol-dichloromethane mixture to provide colorless (white) crystals of 1-(1,1-dimethylethyl)-1H-imidazo[4,5-c]-quinolin-4-ol, m.p. greater than 300° C. Analysis: Calculated for $C_{14}H_{15}N_3O$: % C, 69.7; % H, 6.3; % N, 17.4; Found: % C, 69.5; % H, 6.3; % N, 17.3.

Step B

A mixture of 13 g (0.054 mole) of 1-(1,1-dimethylethyl)-1H-imidazo[4,5-c]quinolin-4-ol and 100 mL of 6N hydrochloric acid was heated at reflux for about 30 minutes. The mixture was allowed to cool to about 20° C., then the solid was separated by filtration. The solid was slurred in dilute ammonium hydroxide, then separated by filtration, washed with water and dried. The solid was slurred in ethanol and heated on a steam bath to evaporate the ethanol. The white solid residue was 1H-imidazo[4,5-c]quinolin-4-ol.

Step C

To a mixture of 7.7 g (0.0416 mole) of 1H-imidazo[4,5-c]quinolin-4-ol and 50 mL of N,N-dimethylformamide was added in small portions 12 mL (0.13 mole) of phosphorus oxychloride. The mixture was heated on a steam bath for 1.5 hour, poured onto ice and basified with concentrated ammonium hydroxide. The solid precipitate was separated by filtration, washed with water and dried to provide 4-chloro-1H-imidazo[4,5-]quinoline as a tan powder corresponding to the product of Example 18.

EXAMPLE 30

Preparation of a Compound of Formula XVIII

Step A

Fuming nitric acid (262 mL) was added at about 20° C. to a suspension of 4-hydroxy-2(1H)-quinolinone (1.0 Kg) in acetic acid (7.57 L). The mixture was heated at 40° C. for 2.5 h. The resulting solution was cooled to about 20° C. and poured into 8 L of water. The resulting solution was stirred for 20 min, filtered, washed with water until the filtrate was neutral, and dried. The product 4-hydroxy-3-nitro-2(1H)-quinolinone was isolated in 98% yield and showed only one spot upon analysis by thin layer chromatography (silica gel, 20:80 (V/V) chloroform in methanol).

Step B

Phosphorous oxychloride (50 mL) was added over a period of 1 hour to a mixture of 4-hydroxy-3-nitro-2(1H)-quinolinone (10 g) and pyridine (10 mL), keeping the temperature below 50° C. The suspension was heated at reflux for 5 h, during which time 40 mL of phosphorus oxychloride was removed by distillation. Cold water was slowly added to the mixture, maintaining temperature below 20° C. The resulting aqueous solution was extracted with chloroform. The extracts were dried over sodium sulfate and concentrated. The solid product 2,4-dichloro-3-nitroquinoline was recrystallized from petroleum ether.

Step C 2,4-dichloro-3-nitroquinoline (5.3 g, 0.218 mol) was combined with 75 mL of 15 percent ammonia in methanol and the mixture was heated at about 45° C. for about 4 hours. The reaction mixture was cooled to room temperature, and the precipitated product was removed by filtration. The volume of methanol was reduced to about 35 mL, and the precipitated product was removed by filtration. The volume of methanol was then reduced to about 10 mL and the precipitated product was again removed by filtration. The combined solids were stirred in aqueous sodium bicarbonate, filtered, and dried to afford a solid product 4-amino-2-chloro-3-nitroquinoline.

Step D 4-amino-2-chloro-3-nitroquinoline (5 g, 0.0224 mol) was combined with ethyl acetate (300 mL), magnesium sulfate (1 g), and 5% Pt/C (0.5 g). The mixture was hydrogenerated on a Parr apparatus until no further uptake of hydrogen was observed. The resulting mixture was filtered and the solvent was removed at reduced pressure to afford a tan solid product 3,4-diamino-2-chloroquinoline.

What is claimed is:

1. A compound of the formula:

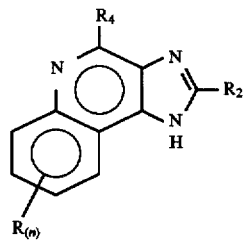

wherein $R_2$ is selected from the group consisting of benzyl, (phenyl)ethyl and phenyl, the benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when the benzene ring is substituted by two such moieties, then the moieties together contain no more than 6 carbon atoms;

$R_4$ is selected from the group consisting of —Cl and —OH; and each R is independently selected from the group consisting of alkoxy of one to about four carbon atoms, halogen, and alkyl of one to about four carbon atoms, and n is an integer from zero to 2, with the proviso that if n is 2, then said R groups together contain no more than 6 carbon atoms.

* * * * *